United States Patent
Yang

(10) Patent No.: US 8,506,529 B1
(45) Date of Patent: Aug. 13, 2013

(54) METHOD AND STRUCTURE OF MONOLITHETICALLY INTEGRATED MICRONEEDLE BIOCHIP

(75) Inventor: Xiao (Charles) Yang, Cupertino, CA (US)

(73) Assignee: MCube Inc., San Jose, CA (US)

( * ) Notice: Subject to any disclaimer, the term of this patent is extended or adjusted under 35 U.S.C. 154(b) by 712 days.

(21) Appl. No.: 12/634,638

(22) Filed: Dec. 9, 2009

Related U.S. Application Data

(63) Continuation of application No. 12/499,029, filed on Jul. 7, 2009, now abandoned.

(60) Provisional application No. 61/079,110, filed on Jul. 8, 2008.

(51) Int. Cl.
*A61F 7/12* (2006.01)

(52) U.S. Cl.
USPC .......................................................... 604/114

(58) Field of Classification Search
USPC ............... 604/114, 118, 132, 133, 891.1, 272
See application file for complete search history.

(56) References Cited

U.S. PATENT DOCUMENTS

| | | | |
|---|---|---|---|
| 5,090,963 A * | 2/1992 | Gross et al. | 604/132 |
| 5,135,499 A * | 8/1992 | Tafani et al. | 604/141 |
| 7,887,508 B2 * | 2/2011 | Meng et al. | 604/114 |
| 2004/0068224 A1 * | 4/2004 | Couvillon et al. | 604/67 |
| 2008/0039792 A1 * | 2/2008 | Meng et al. | 604/114 |
| 2010/0075481 A1 | 3/2010 | Yang | |

* cited by examiner

*Primary Examiner* — Nicholas Lucchesi
*Assistant Examiner* — Diva K Chander
(74) *Attorney, Agent, or Firm* — Kilpatrick Townsend & Stockton LLP

(57) ABSTRACT

The present invention provides a method and device using CMOS and MEMS fabrication techniques for making an integrated microneedle device with integrated circuits. Merely by way of example, the technology can be applied to bio and chemical sensing, and other bioMEMS applications. In some embodiments, the integrated circuits are completed using standard IC processes. For example, an array of microneedles are fabricated on top of the IC substrate followed by formation of micro fluidic channels in the substrate. On-chip integrated circuits enable real-time sensing and intelligent drug delivery.

8 Claims, 5 Drawing Sheets

METHOD AND STRUCTURE OF MONOLITHETICALLY INTEGRATED MICRONEEDLE BIOCHIP

CROSS-REFERENCES TO RELATED APPLICATIONS

This application is a continuation of U.S. patent application Ser. No. 12/499,029 filed Jul. 7, 2009 now abandoned which claims priority to U.S. Provisional Patent Application Ser. No. 61/079,110 filed Jul. 8, 2008, commonly assigned and incorporated by reference in its entirety for all purposes herein.

BACKGROUND OF THE INVENTION

The present invention is related to microneedle devices. More particularly, the present invention provides a method and device using CMOS and MEMS fabrication techniques for making an integrated microneedle device with integrated circuits. Merely by way of example, the technology can be applied to bio and chemical sensing, other bioMEMS applications.

Microneedle has been proposed for sensing of biomedical conditions and drug delivery. The conventional microneedle is believed to be promising and is likely to replace conventional invasive blood sampling and macro needle injections. In sensing applications, microneedle device enables sampling of the body analyte at the Stratum Corneum and Viable Epidermis interface through extraction of interstitial fluid. The bioanalytes could be detected vary from monitoring of glucose, lactate to smoking products like nicotine, cotinine etc.

Unfortunately, the conventional microneedle technologies have various limitations. Sensing and drug delivery use two discrete devices, which are separate and apart from each other. The separate devices often lead to difficulty in use and efficiencies. Additionally, the conventional microneedle device is typically fabricated using conventional MEMS technology, which is complex and costly. Conventional MEMS technology also is a stand alone operation and cannot be integrated with other processes. Accordingly, microneedle technologies have limited use and are only found in research and development. These and other limitations are described throughout the present specification and more particularly below.

Thus, it is desirable to improve microneedle technology.

BRIEF SUMMARY OF THE INVENTION

The present invention is related to microneedle devices. More particularly, the present invention provides a method and device using CMOS and MEMS fabrication techniques for making an integrated microneedle device with integrated circuits. Merely by way of example, the technology can be applied to bio and chemical sensing, other bioMEMS applications.

First, the integrated circuits are completed using standard IC processes. An array of microneedles are fabricated on top of the IC substrate followed by formation of micro fluidic channels in the substrate. On-chip integrated circuits enable real-time sensing and intelligent drug delivery.

In an embodiment, the present invention includes an integrated biosensor and circuit device. The device can include a CMOS integrated circuit layer overlying a surface region of a semiconductor substrate. One or more dielectric layers and a fluid chamber region can overlie the CMOS integrated circuit layer. One or more needle devices can be in communication with the fluid chamber region while also overlying the CMOS integrated circuit layer.

In a specific embodiment, each of the needle devices can have a fluid channel therein. The fluid channel can extend from a base region to a vicinity of a tip region. The tip region can range from a few nanometers to about microns. The tip can be made of a material selected from silicon, titanium nitride, titanium, or stainless steel. One or more sensing devices can be coupled to the needle devices. These sensing devices can be provided from the CMOS integrated circuit device layer. The sensing devices can be provided in the fluid chamber In a specific embodiment, the one or more needle devices can include a plurality of needle devices configured in an N by M array, wherein M is an integer greater than 2. The device can further include a pump device and/or a drug source in communication with the fluid chamber. The device can also further include one or more actuator devices in fluid communication with the fluid chamber. These actuator devices can be coupled to one or more drive devices. These drive devices can be selected from a group consisting of one or more electrodes, one or more PZT devices, one or more diaphragm devices, one or more thermal devices or one or more magnetic devices. Those of ordinary skill in the art will recognize other variations, modifications, and alternatives.

BRIEF DESCRIPTION OF THE DRAWINGS

The following diagrams are merely examples, which should not unduly limit the scope of the claims herein. One of ordinary skill in the art would recognize many other variations, modifications, and alternatives. It is also understood that the examples and embodiments described herein are for illustrative purposes only and that various modifications or changes in light thereof will be suggested to persons skilled in the art and are to be included within the spirit and purview of this process and scope of the appended claims.

DETAILED DESCRIPTION OF THE INVENTION

The present invention is related to microneedle devices. More particularly, the present invention provides a method and device using CMOS and MEMS fabrication techniques for making an integrated microneedle device with integrated circuits. Merely by way of example, the technology can be applied to bio and chemical sensing, other bioMEMS applications.

Figure 1:
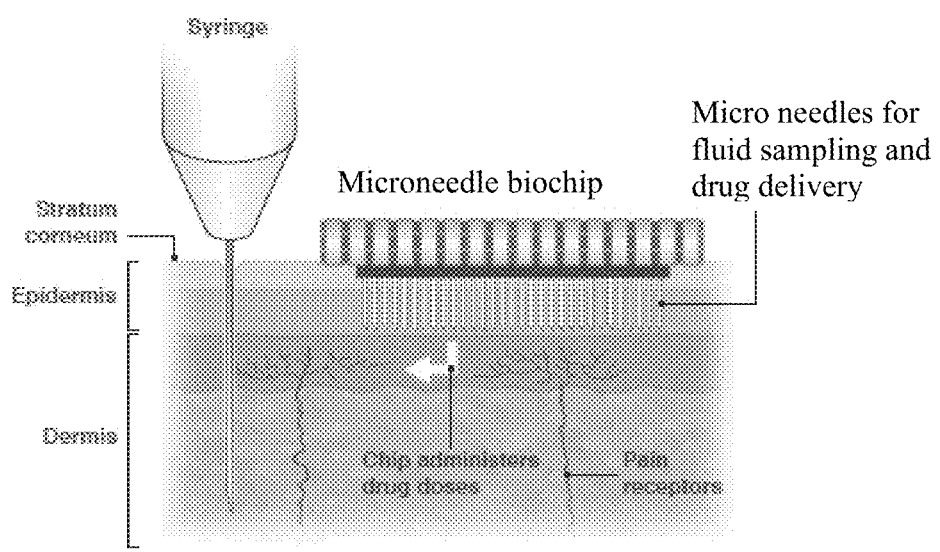
FIG. 1 is a simplified cross section diagram of a microneedle biochip according to an embodiment of the present invention.

FIG. 1 is a simplified cross section diagram of a microneedle biochip according to one embodiment of the present invention. As depicted, the microneedles penetrate only the Stratum Corneum and Viable Epidermis layers, whereas the conventional macro needle penetrates to Dermis layer where pain receptor nerves reside. The microneedle chip samples body analyte through extraction of interstitial fluid through the microneedles for on-chip sensing. The microneedles are also used for real-time drug delivery based on the sensing results.

Figure 2:
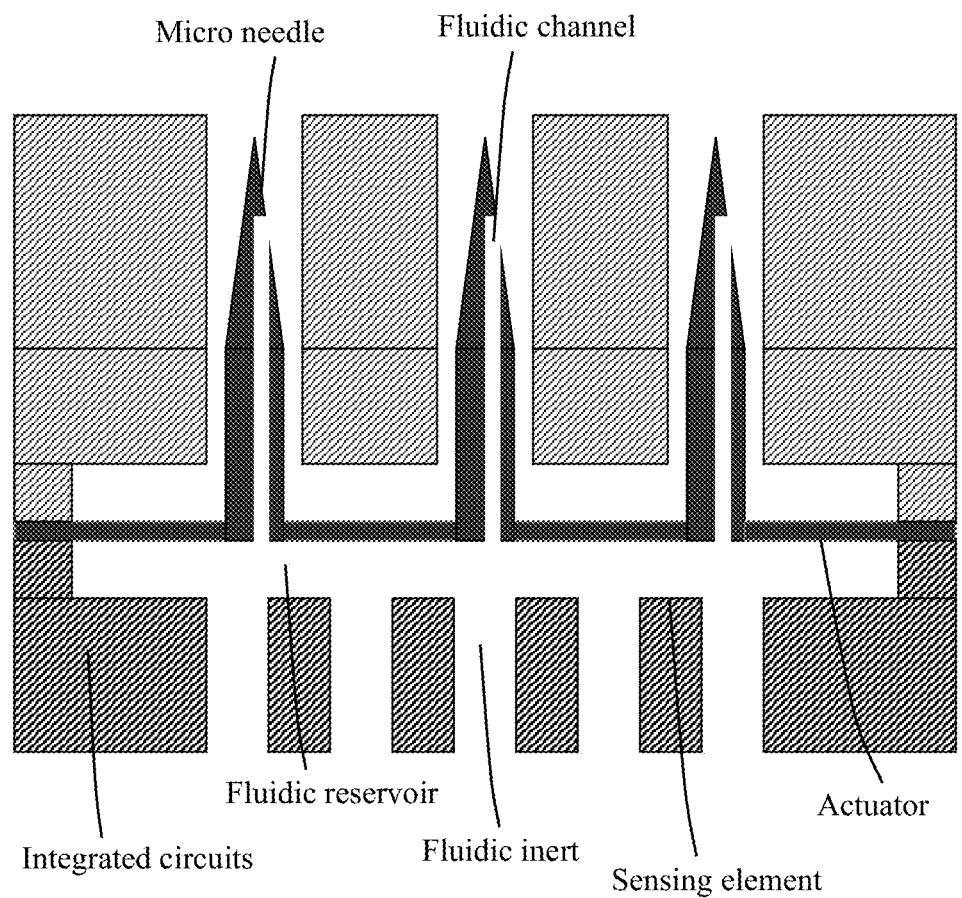
FIG. 2 is a simplified cross section diagram of components of a microneedle biochip according to an embodiment of the present invention.

FIG. 2 is a simplified cross section diagram of components of a microneedle biochip according to one embodiment of the present invention. As depicted, the microneedle device is fabricated on an IC substrate. The microneedles are sharp tips with micro fluidic channels inside. The microneedles are coupled to actuators that move microneedles in out-of-plane movement. Fluidic reservoir is fabricated in the IC substrate as sample chamber for sensing and storage for fluidic medicine for drug delivery. Fluidic channels are fabricated in the IC substrate for controlling fluidic medicine. Sensing elements are built on-chip to detect body analyte extracted by the microneedles. In one embodiment, glucose from the interstitial fluid of the epidermis diffuses through microneedles into the reservoir. An integrated enzyme-based electrochemical glucose sensor measures the glucose concentration. On-chip integrated circuits enable real-time sensing and intelligent drug delivery.

Figure 3:
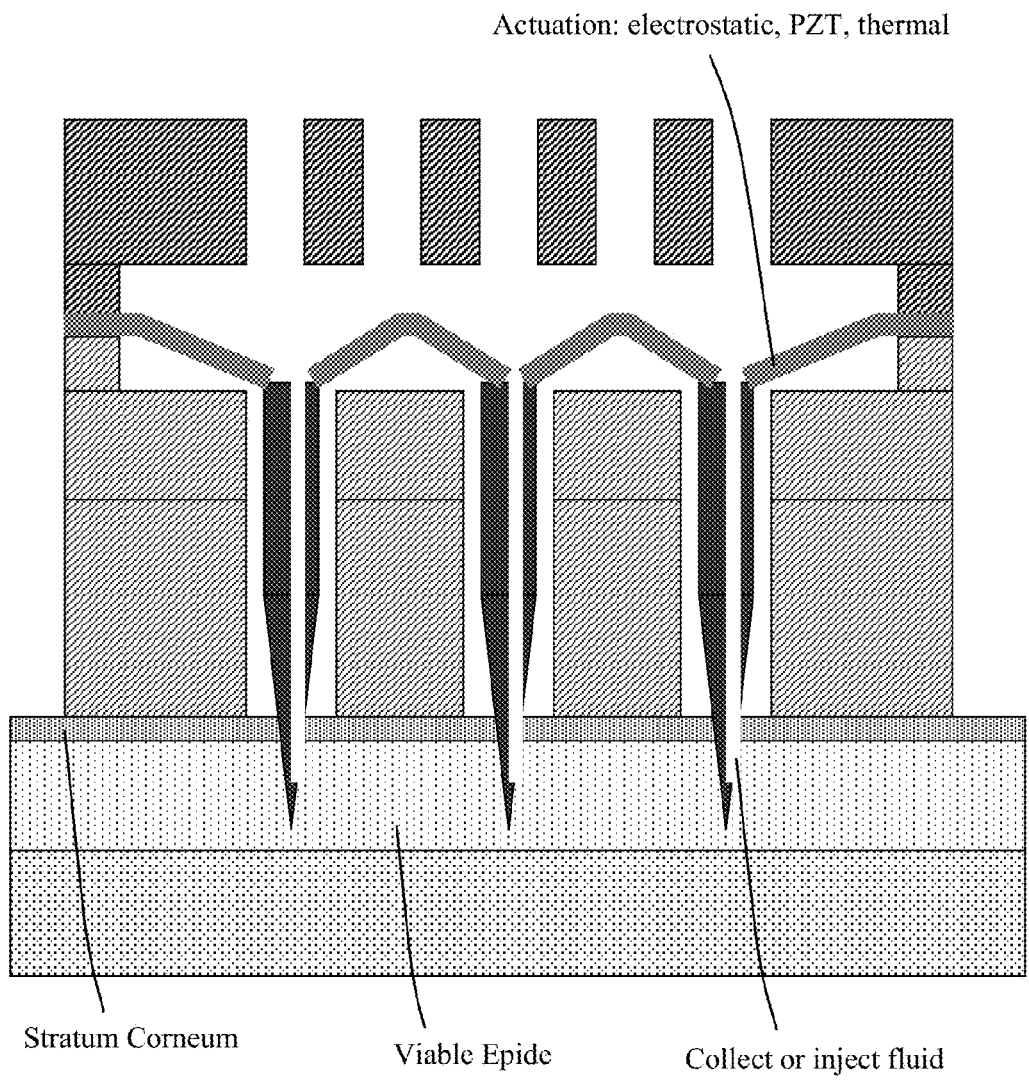
FIG. 3 is a simplified cross section diagram of components of a microneedle biochip according to an embodiment of the present invention.

FIG. 3 is a simplified cross section diagram of components of a microneedle biochip according to one embodiment of the present invention. As depicted, the microneedle device is in contact with a skin. The actuators move the microneedles in an out-of-plane displacement that penetrate into the Stratum Corneum and Viable Epide layers. The actuation methods include not limited to: electrostatic, PZT, thermal. The micro fluidic channels in the microneedles extract interstitial fluid for on-chip sensing and are also used for drug delivery into the body. The depth of penetration can be adjusted intelligent by the on-chip integrated circuits for various skin thickness and sensing or drug delivery applications.

Figure 4:
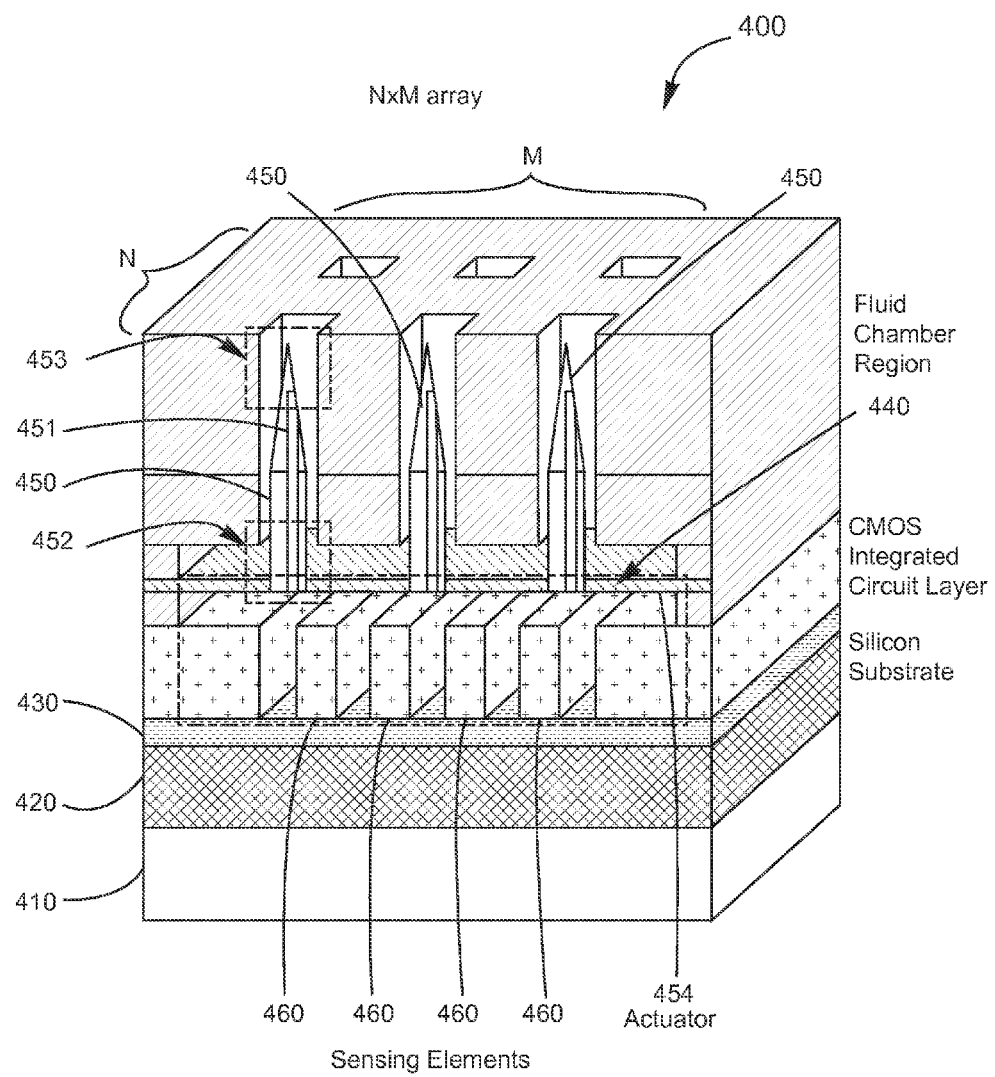
FIG. 4 is a simplified cross section diagram of a microneedle biochip according to an embodiment of the present invention.

FIG. 4 is a simplified cross section diagram of a microneedle biochip according to an embodiment of the present invention. In an embodiment, the present invention includes an integrated biosensor and circuit device 400. The device 400 can include a CMOS integrated circuit layer 420 overlying a surface region of a semiconductor substrate 410. One or more dielectric layers 430 and a fluid chamber region 440 can overlie the CMOS integrated circuit layer 420. One or more needle devices 450 can be in communication with the fluid chamber region 440 while also overlying the CMOS integrated circuit layer 420.

In an embodiment, the dielectric layers 430 can include oxide and nitride material deposited on top of a top metal layer of the fully processed IC wafer, including the substrate and the CMOS integrated circuit layer. The dielectric layers 430 can be patterned to form a structure that provides anchor points for a mechanical structure formed above.

In a specific embodiment, each of the needle devices 450 can have a fluid channel 451 therein. The fluid channel 451 can extend from a base region 452 to a vicinity of a tip region 453. The tip region 453 can range from a few nanometers to about microns. The tip can be made of a material selected from silicon, titanium nitride, titanium, or stainless steel. One or more sensing devices 460 can be coupled to the needle devices 450. These sensing devices 460 can be provided from the CMOS integrated circuit device layer 420. The sensing devices 460 can be provided in the fluid chamber 440.

In a specific embodiment, the one or more needle devices 450 can include a plurality of needle devices configured in an N by M array, wherein M is an integer greater than 2. The one or more needle devices can be supported by one or more members integrally formed overlying the CMOS integrated circuit device layer. The device 400 can further include a pump device 470 and/or a drug source 480 in communication with the fluid chamber. The device 400 can also further include one or more actuator devices 454 in fluid communication with the fluid chamber 440. These actuator devices 454 can be coupled to one or more drive devices. These drive devices can be selected from a group consisting of one or more electrodes, one or more PZT devices, one or more diaphragm devices, one or more thermal devices or one or more magnetic devices. Those of ordinary skill in the art will recognize other variations, modifications, and alternatives.

Figure 5:
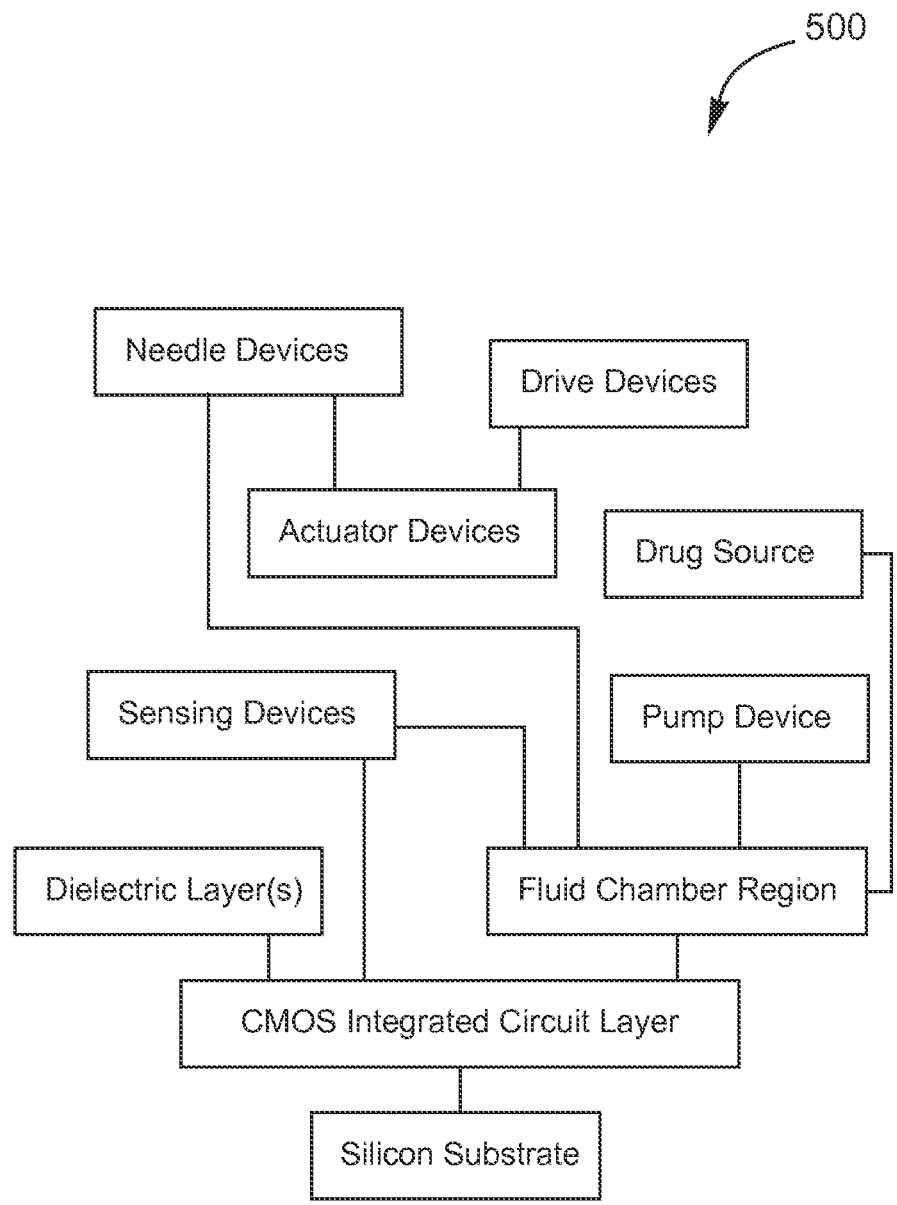
FIG. 5 is a simplified block diagram of a microneedle biochip according to an embodiment of the present invention.

FIG. 5 is a simplified block diagram of a microneedle biochip according to an embodiment of the present invention. In an embodiment, the present invention includes an integrated biosensor and circuit device 500. The device 500 can include a CMOS integrated circuit layer overlying a surface region of a semiconductor substrate. One or more dielectric layers and a fluid chamber region can overlie the CMOS integrated circuit layer. One or more needle devices can be in communication with the fluid chamber region while also overlying the CMOS integrated circuit layer.

In a specific embodiment, each of the needle devices can have a fluid channel therein. The fluid channel can extend from a base region to a vicinity of a tip region. The tip region can range from a few nanometers to about microns. The tip can be made of a material selected from silicon, titanium nitride, titanium, or stainless steel. One or more sensing devices can be coupled to the needle devices. These sensing devices can be provided from the CMOS integrated circuit device layer. The sensing devices can be provided in the fluid chamber and can be anchored to the dielectric layer.

In a specific embodiment, the one or more needle devices can include a plurality of needle devices configured in an N by M array, wherein M is an integer greater than 2. The device 500 can further include a pump device and/or a drug source in communication with the fluid chamber. The device 500 can also further include one or more actuator devices in fluid communication with the fluid chamber. These actuator devices can be coupled to one or more drive devices. These drive devices can be selected from a group consisting of one or more electrodes, one or more PZT devices, one or more diaphragm devices, one or more thermal devices or one or more magnetic devices. Of course, those of ordinary skill in the art will recognize other variations, modifications, and alternatives.

It is also understood that the examples and embodiments described herein are for illustrative purposes only and that various modifications or changes in light thereof will be suggested to persons skilled in the art and are to be included within the spirit and purview of this application and scope of the appended claims.

What is claimed is:
1. An integrated biosensor and circuit device comprising:
a semiconductor substrate comprising a surface region;
a CMOS integrated circuit layer overlying the surface region;
one or more dielectric layers overlying the CMOS integrated circuit layer;
a fluid chamber region overlying the CMOS integrated circuit layer;
one or more needle devices in communication with the fluid chamber region, the one or more needle devices overlying the CMOS integrated circuit layer, each of the needle devices having fluid channel therein, the fluid channel extending from a base region to a vicinity of a tip region, the one or more needle devices being configured to be supported by one or more members integrally formed overlying the CMOS integrated circuit device layer; and one or more sensing devices coupled to the one or more needle devices, the one or more sensing devices provided from the CMOS integrated circuit device layer.

2. The device of claim 1 wherein the tip region ranges from a few nanometers to about microns.

3. The device of claim 1 wherein the one or more sensing devices are provided in the fluid chamber.

4. The device of claim 1 wherein the tip is made of a material selected from silicon, titanium nitride, titanium, or stainless steel.

5. The device of claim 1 wherein the one or more needle devices comprise a plurality of needle devices configured in an N by M array, wherein M is an integer greater than 2.

6. The device of claim 1 further comprising a pump device in communication with the fluid chamber.

7. The device of claim 1 further comprising a drug source in communication with the fluid chamber.

8. The device of claim 1 further comprising one or more actuator devices in fluid communication with the fluid chamber, the one or more actuator devices being coupled to one or more drive devices, the one or more drive devices being selected from a group consisting of one or more electrodes, one or more PZT devices, one or more diaphragm devices, one or more thermal devices, or one or more magnetic devices.

\* \* \* \* \*